United States Patent
Schroder

(10) Patent No.: US 6,749,579 B1
(45) Date of Patent: Jun. 15, 2004

(54) TRACTION GARMENT

(76) Inventor: Mitchell J. Schroder, 4977 E. 169th St., Noblesville, IN (US) 46060

( * ) Notice: Subject to any disclaimer, the term of this patent is extended or adjusted under 35 U.S.C. 154(b) by 53 days.

(21) Appl. No.: 10/213,855

(22) Filed: Aug. 7, 2002

(51) Int. Cl.$^7$ .................................................. A61F 5/00
(52) U.S. Cl. ............................. 602/36; 602/32; 602/19; 2/467
(58) Field of Search ............................... 602/19, 32, 36, 602/40, 60, 5; 2/467, 462; 128/976

(56) References Cited

U.S. PATENT DOCUMENTS

| | | | |
|---|---|---|---|
| 1,589,670 A | * 6/1926 | Vartia | 602/36 |
| 1,722,205 A | * 7/1929 | Freund | 2/44 |
| 1,755,641 A | * 4/1930 | Foulke | 602/19 |
| 2,835,247 A | 5/1958 | Stabholc | |
| 2,886,031 A | * 5/1959 | Robbins | 602/19 |
| 3,548,817 A | 12/1970 | Mittasch | |
| 3,799,156 A | 3/1974 | Gurkin | |
| 3,889,664 A | 6/1975 | Heuser et al. | |
| 3,926,182 A | 12/1975 | Stabholz | |
| 4,135,503 A | 1/1979 | Romano | |
| 4,541,419 A | 9/1985 | Osawa | |
| 4,715,362 A | * 12/1987 | Scott | 602/36 |
| 4,721,102 A | * 1/1988 | Pethybridge | 602/19 |
| 4,907,575 A | 3/1990 | Satterthwaite | |
| 5,045,313 A | 9/1991 | Frenkel et al. | |
| 5,111,807 A | 5/1992 | Spahn et al. | |
| 5,188,585 A | 2/1993 | Peters | |
| 5,228,458 A | 7/1993 | Ciacca | |
| 5,403,266 A | 4/1995 | Bragg et al. | |
| 5,437,617 A | * 8/1995 | Heinz et al. | 602/19 |
| 5,462,518 A | 10/1995 | Hatley et al. | |
| 5,599,286 A | * 2/1997 | Labelle et al. | 602/19 |
| 5,704,904 A | 1/1998 | Dunfee | |
| 5,724,993 A | 3/1998 | Dunfee | |
| 5,823,982 A | * 10/1998 | Park | 602/36 |
| 5,840,051 A | 11/1998 | Towsley | |
| 5,916,188 A | * 6/1999 | Ousdal | 602/32 |
| 5,950,628 A | 9/1999 | Dunfee | |
| 6,045,525 A | 4/2000 | Chitwood | |
| 6,146,345 A | 11/2000 | Mignard | |
| 6,280,405 B1 | 8/2001 | Broselid | |
| 6,450,926 B1 | * 9/2002 | McKernan | 482/91 |
| 6,635,025 B1 | * 10/2003 | Reinecke et al. | 602/19 |

* cited by examiner

Primary Examiner—Henry Bennett
Assistant Examiner—Amanda Flynn
(74) Attorney, Agent, or Firm—C. John Brannon; Bingham McHale LLP

(57) ABSTRACT

A traction belt, including a first elongated portion, a second elongated portion oriented generally parallel to the first elongated portion and connected thereto, a first plurality of biasing members operationally connected to the first elongated portion, and a second plurality of biasing members operationally connected to the second elongated portion. Each biasing member is oriented generally perpendicular to a respective elongated portion. Each biasing member is adapted to provide a biasing force through a respective elongated portion.

12 Claims, 3 Drawing Sheets

//////

TRACTION GARMENT

BACKGROUND OF THE INVENTION

Traction has long been the treatment of choice for certain injuries to the lumbar, sacral and/or pelvic regions of the body. Traction involves applying a tensile or traction force to these areas to relieve a portion of the compressive load on the spine to alleviate pain and allow proper healing of the injuries. Traditionally, traction has been applied through stationary means, such as traction beds, that require the patient to remain immobile and unproductive for extended periods of time. There are several disadvantages to these traditional stationary traction devices. For example, during prolonged convalescence, the immobile patient is prone to atrophy of his non-injured musculature as well as to weight gain arising from his sudden immobility. Further, otherwise active people are especially susceptible to boredom that at best is merely bothersome and at worst can lead to clinical depression and/or the premature abandonment of the traction treatment. This, in turn, readily leads to reinjury and even longer convalescence.

While some advances have been made in the field of ambulatory traction devices, those currently known all suffer from the same drawbacks of being bulky, cumbersome, and limited in their ability to provide effective traction forces and attendant support. For example, U.S. Pat. No. 3,889,664 to Heuser et al.; U.S. Pat. No. 5,462,518 to Hatley et al.; and U.S. Pat. No. 6,280,405 to Brosleid each disclose ambulatory traction apparati featuring pairs of elongated structural members as part of the worn apparatus. These members extend to lengths of about a foot or more, rendering the traction apparatus heavy, bulky and cumbersome and unsuited for use while sitting or transitioning between sitting and standing. U.S. Pat. No. 2,835,247 to Stabholc; U.S. Pat. No. 3,548,817 to Mittasch; and U.S. Pat. No. 4,907,575 to Satterthwaite each disclose ambulatory traction devices having a pair of oppositely disposed traction force applicators connected to a waist-worn belt. While less bulky than the aforementioned prior art patents, these devices only provide bilaterally disposed traction to the patient and are insufficient for providing injury-specific traction. Further, these devices do not effectively limit or retard undesired movements such as twisting or bending.

There therefore remains a need for a traction device that is non-stationary or ambulatory and provides injury-specific traction while restricting unwanted and potentially injurious motions. The present invention addresses this need.

SUMMARY OF THE INVENTION

The present invention relates to a method and apparatus for providing traction to an ambulatory or non-stationary traction patient. One object of the present invention is to provide an improved traction applicator. Related objects and advantages of the present invention will be apparent from the following description.

DESCRIPTION OF THE PREFERRED EMBODIMENTS

Figure 1:
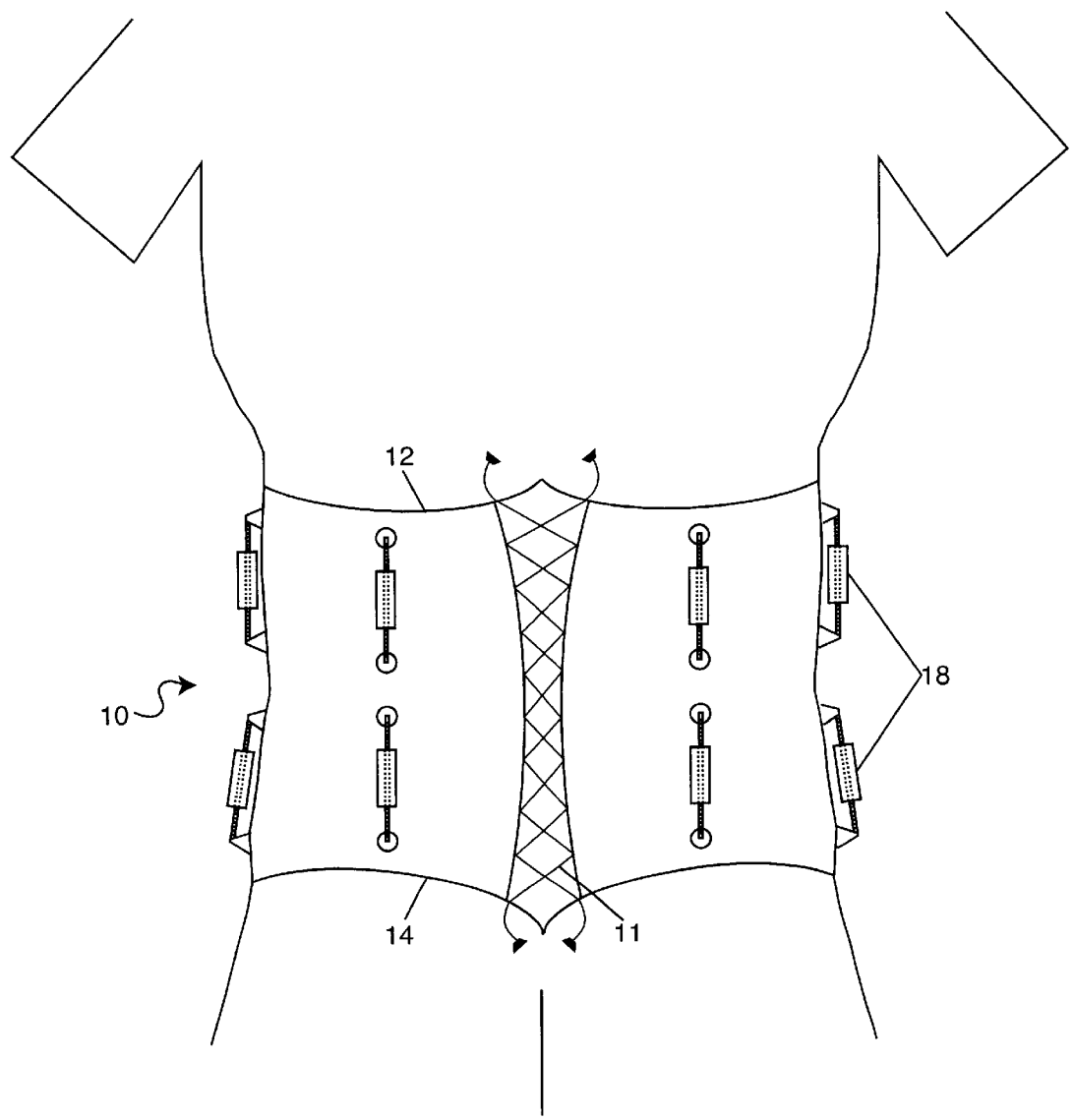
FIG. 1 is a rear elevational view of a first embodiment of the present invention, a garment for providing traction as worn by an ambulatory patient.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 2:
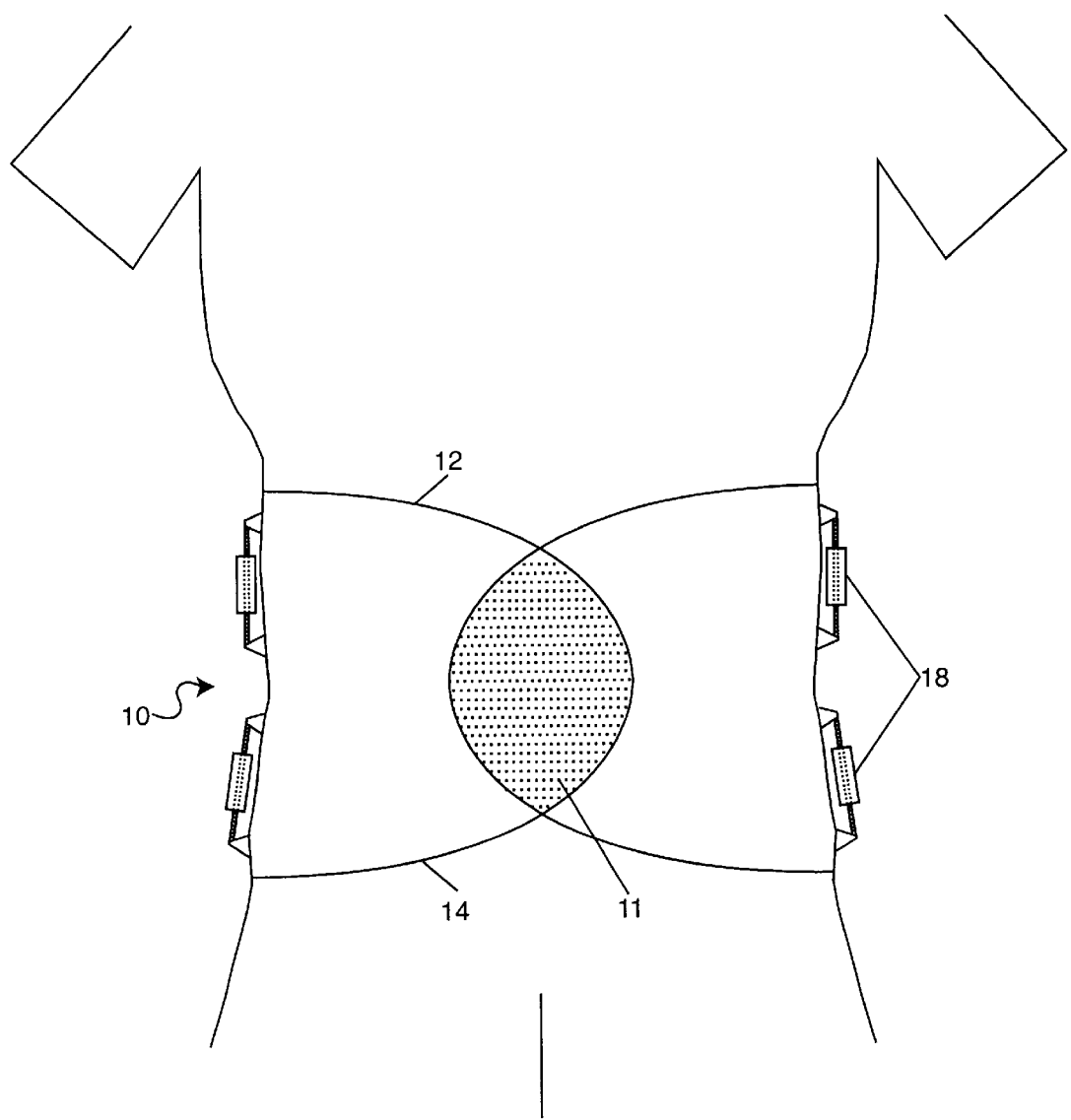
FIG. 2 is a front elevational view of the embodiment of FIG. 1.
Figure 3:
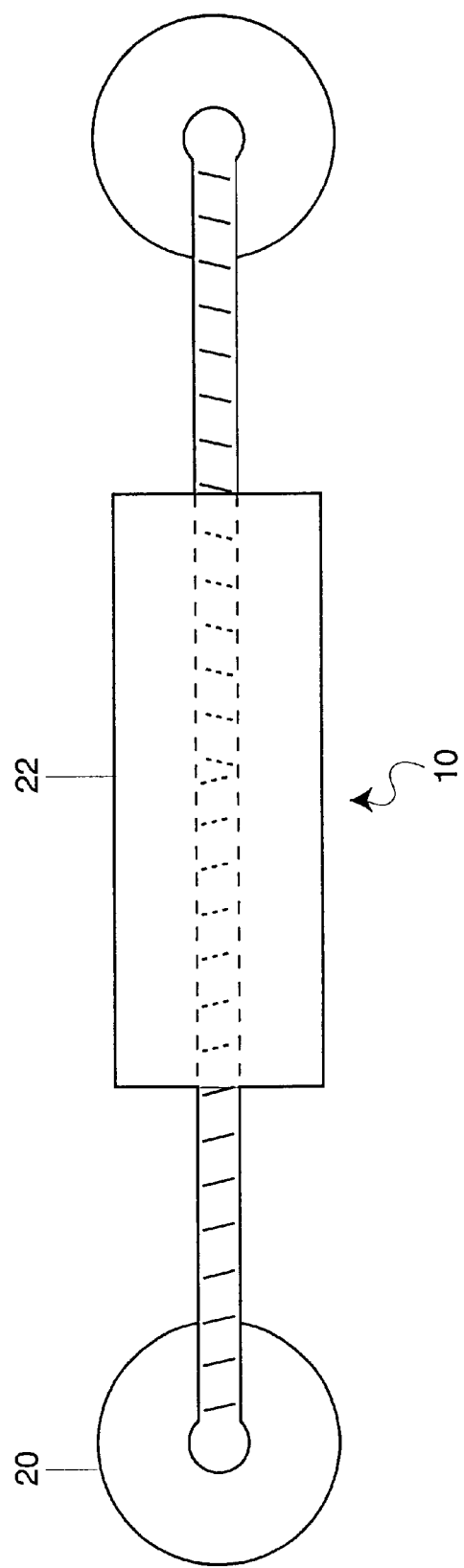
FIG. 3 is an enlarged partial view of a biasing member of the embodiment of FIG. 1.

A first embodiment of the present invention is illustrated in FIGS. 1–3. The invention comprises a garment 10 for treating muscle injuries with traction. The garment 10 is preferably a belt or corset adapted to extend around the waist or torso to snugly engage the sacral, lumbar, and/or pelvic regions of a traction patient. However, the garment 10 is also contemplated as having any convenient configuration. The garment 10 includes an upper elongated portion 12 and a lower elongated portion 14 as well as a plurality of biasing members or tension spreaders 18 connected to each elongated portion 12, 14.

The garment 10, including the biasing members 18, is preferably sufficiently stiff or rigid so as to restrict undesired movement of the patient, such as side-bending or waist-rotation. Also preferably, the garment material is sufficiently pliable such that the biasing force generated by the biasing members 18 is substantially completely transmitted through the garment 10 to the patient.

The garment 10 is essentially a belt that may be looped around a patient and secured to itself such that the patient is snugly engaged by the garment 10. The garment 10 further includes a fastening assembly 11 for connecting the garment to itself, such as lace and eye type connectors (see FIG. 1), hook-and-loop type connectors (hooks attached to one end, mating loops to the other—see FIG.2), tongue and eye (the tongue connected to one end and eye notches formed through the other), or the like. The garment 10 is preferably substantially formed of a strong, flexible material such as leather or a polymer, and is more preferably substantially formed of nylon.

FIG. 3 illustrates a first embodiment biasing member 18 in more detail. Each biasing member 18 includes a pair of anchors 20 connected to the garment 10. Each pair of anchors 20 is connected by a rigid member 22 of variable length, such as a tension screw, turnbuckle, or the like. The biasing members 18 are positioned around the garment 10 and aligned in a generally vertical direction (as referenced to a patient wearing the garment while standing), such that they may be adjusted to provide a desired amount of tension to the injured area of the patient requiring traction. Preferably, a first linear array of biasing members 18 is connected to the upper portion 12 and a second linear array of biasing members is connected to the lower portion 14.

In operation, a traction patient dons the garment 10 and positions the biasing members 18 to be substantially adjacent those injured body regions requiring traction. The patient then adjusts the biasing force of each respective biasing member 18 to provide optimal biasing force. In other words, the biasing members 18 nearest the injured regions are adjusted to provide substantial traction and the biasing members 18 removed from the injured regions are adjusted to provide less or no traction. Preferably, the biasing members 18 are positioned to substantially encircle the sacral-lumbar region of the patient and more preferably about half of the biasing members 18 are connected to the upper portion 12 and about half are connected to the lower portion 14. In other words, about half of the biasing members 18 generally positioned at a first, upper latitude encircling the patient and about half of the biasing members 18 are generally positioned at a second, lower latitude parallel (the two latitudes are substantially non-coextensive insofar as they do not intersect).

Other contemplated embodiments of the present invention include garments 10 having three or more parallel portions, each with biasing members 18 attached. Additionally, the garment 10 may be sized such that it can be worn around the mid- or upper-torso or even around the neck to provide traction at any desired spinal location.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A garment for a traction patient, comprising:
   a patient-encircling band having an upper portion and a lower portion;
   a fastener connected to the band and adapted to keep the band snugly encircled about the patient;
   a first plurality of spreaders operationally connected to the band and distributed about the upper portion; and
   a second plurality of spreaders operationally connected to the band and distributed about the lower portion;
   wherein the first plurality of spreaders is positioned at a first latitude;
   wherein the second plurality of spreaders is positioned at a second latitude;
   wherein the first and second latitudes are non-coextensive,
   wherein each spreader further comprises respective elongated adjustable biasing member extending between a respective pair of anchors;
   wherein each spreader may generate a biasing force between the respective pair of anchors; and
   wherein each spreader may be independently adjusted regarding the amount of biasing force generated.

2. The garment of claim 1 wherein each respective spreader is connected to the band between a respective pair of anchors, and wherein each respective pair of anchors is adapted to transmit biasing force through the band to the patient.

3. The garment of claim 1 wherein each spreader further comprises a turnbuckle operationally connected between a respective pair of anchors.

4. The garment of claim 1 wherein the band is sufficiently stiff to inhibit the patient from engaging in waist-twisting and waist-bending movements.

5. A traction belt, comprising:
   a first elongated portion;
   a second elongated portion oriented generally parallel to the first elongated portion and connected thereto;
   a first plurality of biasing members operationally connected to the first elongated portion; and
   a second plurality of biasing members operationally connected to the second elongated portion;
   wherein the first plurality of spreaders is non-coextensive with the second plurality of spreaders;
   wherein each biasing member is oriented generally perpendicular to a respective elongated portion; and
   wherein each biasing member is adapted to provide a biasing force through a respective elongated portion.

6. The traction belt of claim 5 wherein each respective biasing member is connected to a respective elongated portion between a respective pair of anchor means for transmitting biasing force through the belt to the patient.

7. The traction belt of claim 6 wherein each biasing member further comprises a turnbuckle operationally connected between the anchor means.

8. The traction belt of claim 5 wherein the elongated portions engage a patient to prevent the patient from engaging in waist-twisting and waist-bending movements.

9. A mobile traction unit, comprising:
   a first elongated upper portion and a second elongated lower portion coupled together and defining a body encircling band;
   a plurality of upper biasing members operationally connected to the upper portion;
   a plurality of lower biasing members operationally connected to the lower portion;
   wherein each plurality of biasing members is distributed generally linearly and positioned generally parallel to the body-encircling band;
   wherein each respective biasing member is oriented generally perpendicular to the respective elongated portion to which the respective biasing member is attached;
   wherein each respective biasing member is connected to only one band portion;
   wherein the band is adapted to snugly engage a patient; and
   wherein the band is sufficiently pliable to transmit biasing force substantially therethrough; and
   wherein the band is sufficiently stiff to inhibit side-bending or waist-rotation movements when snugly engaging a wearer.

10. A method for providing traction to the sacral-lumbar region of an ambulatory patient, comprising the steps of:
    a) positioning a plurality of individual biasing members substantially adjacent to injured body regions requiring traction; and
    b) adjusting the biasing force of each respective biasing member;
       wherein the biasing members substantially encircle the sacral-lumbar region of the patient;
       wherein each individual biasing member may be independently adjusted;
       wherein a first substantial half of the individual biasing members are generally positioned at a first latitude encircling the patient; and
       wherein a second substantial half of the individual biasing members are generally positioned at a second latitude parallel and substantially non-coextensive with the first latitude.

11. The method of claim 10 further comprising the step of:
    c) inhibiting the patient from engaging in side-twisting and waist-bending motions.

12. The method of claim 10 wherein each biasing member includes a turnbuckle for independent manual biasing force adjustment.

* * * * *